(12) United States Patent
Isawa et al.

(10) Patent No.: US 8,728,459 B2
(45) Date of Patent: May 20, 2014

(54) BACTERIA AND METHOD FOR CONTROLLING PLANT DISEASE USING THE SAME

(75) Inventors: Tsuyoshi Isawa, Tokyo (JP); Michiko Yasuda, Tokyo (JP); Satoshi Shinozaki, Tokyo (JP); Hideo Nakashita, Saitama (JP); Toshiaki Kudo, Saitama (JP)

(73) Assignees: Mayekawa Mfg. Co., Ltd., Tokyo (JP); Riken, Wako-shi (JP)

( * ) Notice: Subject to any disclaimer, the term of this patent is extended or adjusted under 35 U.S.C. 154(b) by 917 days.

(21) Appl. No.: 12/281,560

(22) PCT Filed: Mar. 2, 2007

(86) PCT No.: PCT/JP2007/054624
§ 371 (c)(1),
(2), (4) Date: Dec. 3, 2008

(87) PCT Pub. No.: WO2007/100162
PCT Pub. Date: Sep. 7, 2007

(65) Prior Publication Data
US 2009/0155214 A1   Jun. 18, 2009

(30) Foreign Application Priority Data
Mar. 3, 2006 (JP) ................................. 2006-058483

(51) Int. Cl.
*A61K 35/74* (2006.01)
*A01H 5/00* (2006.01)
*C12N 1/20* (2006.01)
*A01N 63/02* (2006.01)

(52) U.S. Cl.
USPC ....... 424/93.4; 435/252.1; 800/295; 800/306; 800/320; 424/93.3

(58) Field of Classification Search
USPC ............................... 800/301, 302; 435/252.1
See application file for complete search history.

(56) References Cited

U.S. PATENT DOCUMENTS

| | | | |
|---|---|---|---|
| 5,951,978 A | 9/1999 | Red'kina | |
| 6,306,390 B1 | 10/2001 | Narisawa | |
| 2003/0135898 A1 | 7/2003 | Isawa et al. | |
| 2003/0195117 A1* | 10/2003 | Imada et al. | 504/117 |

FOREIGN PATENT DOCUMENTS

| | | |
|---|---|---|
| JP | 5 317092 | 12/1993 |
| JP | 2002 223747 | 8/2002 |
| JP | 2002 531117 | 9/2002 |
| JP | 2003 274779 | 9/2003 |
| JP | 2003 300805 | 10/2003 |
| WO | 98 42823 | 10/1998 |

OTHER PUBLICATIONS

Bashan, Y., and de-Bashan, L.E. Reduction of bacterial spek (*Pseudomonas syringae* pv. tomato) of tomato by combined treatments of plant growth-promoting bacterium, *Azospirillum brasilense*, streptomycin sulfate, and chemo-thermal seed treatment. (2002) Eur. J. Plant Pathol. 108: 821-829.*

Dakora, F.D., Phillips, D.A. Diverse functions of isoflavonoids in legumes transcend anti-microbial definitions of phytoalexins. Physiol. Mol. Plant Pathol. (1996) 49: 1-20.*

Elbeltagy et al. Endophytic colonzation and in planta nitrogen fixation bi a *Herbaspirillum* sp. Isolated from wild rice species. (2001) Appl. Environ. Microbiol. 67: 5285-5293.*

Tsuyoshi Isawa et al., "Bacterial endophytes gave rise to resistance for pests and disease to rice", Abstract of the 14th Annual Meeting for Plant Microbe Interactions, 2004, pp. 48-49, plus cover sheet.

Minamisawa K., et al., "*Azospirillum* sp. B510 Gene for 16S rRNA, Partial Sequence", Retrieved from EBI Accession No. EMBL:AB049111, XP002549098, 2 pages, Mar. 16, 2001.

Adel Elbeltagy, et al., "Endophytic Colonization and in Planta Nitrogen Fixation by a *Herbaspirillum* sp. Isolated from Wild Rice Species", Applied and Environmental Microbiology, XP002549096, vol. 67, No. 11, Nov. 2001, pp. 5285-5293.

Minamisawa K., et al., "*Herbaspirillum* sp. B65 gene for 16S rRNA, Partial Sequence", Retrieved from EBI Accession No. EMBL:AB049103, XP002549099, 2 pages, Mar. 16, 2001.

* cited by examiner

Primary Examiner — Russell Kallis
Assistant Examiner — Steven Bernacki
(74) *Attorney, Agent, or Firm* — Oblon, Spivak, McClelland, Maier & Neustadt, L.L.P.

(57) ABSTRACT

An object of the present invention is to provide a means for imparting resistance against pathogenic fungal, pathogenic bacterial, or pathogenic viral disease to agriculturally useful plants. The present invention relates to a bacterium belonging to the genus *Azospirillum* or the genus *Herbaspirillum* capable of imparting resistance against pathogenic fungal, pathogenic bacterial, or pathogenic viral disease to a host plant by living symbiotically within the plant, a method for controlling plant disease using the bacteria, and plants produced by such method.

14 Claims, 9 Drawing Sheets

Fig. 1-1

```
                                         10        20        30
Azospirillum                    AACGCTGGCGGCATGCCTAACACATGCAAGTCGAAC
                                ::::::::::::::::::::::::::::::::::::
AF521650       AGAGTTTGATCATGGCTCAGAACGAACGCTGGCGGCATGCCTAACACATGCAAGTCGAAC
                       10        20        30        40        50        60

40        50        60        70        80        90
Azospirillum   GATGGCTTCGGCCATAGTGGCGCACGGGTGAGTAACACGTGGGAACCTGCCTTTCGGTTC
               ::  :::::::::: :::::::::::::::::::::::::::::::::::::::::::::
AF521650       GAAGGCTTCGGCCTTAGTGGCGCACGGGTGAGTAACACGTGGGAACCTGCCTTTCGGTTC
                       70        80        90       100       110       120

100       110       120       130       140       150
Azospirillum   GGAATAACGTCTGGAAACGGACGCTAACACCGGATACGCCCTTTTGGGGAAAGTTTACGC
               :::::::::::::::::::: :::::::::::::::::::::::: ::::::::::::::
AF521650       GGAATAACGTCTGGAAATGGACGCTAACACCGGATACGCCCTATTGGGGAAAGTTTACGC
                      130       140       150       160       170       180

160       170       180       190       200       210
Azospirillum   CGAGAGAGGGGCCCGCGTCGGATTAGGTAGTTGGTGTGGTAACGGCGCACCAAGCCGACG
               :::::::::::::::::::::::::::::::::::::::::::::::: :::::::::::
AF521650       CGAGAGAGGGGCCCGCGTCGGATTAGGTAGTTGGTGTGGTAACGGCGCTCCAAGCCGACG
                      190       200       210       220       230       240

220       230       240       250       260       270
Azospirillum   ATCCGTAGCTGGTCTGAGAGGATGATCAGCCACACTGGGACTGAGACACGGCCCAGACTC
               ::::::::::::::::::::::::::::::::::::::::::::::::::::::::::::
AF521650       ATCCGTAGCTGGTCTGAGAGGATGATCAGCCACACTGGGACTGAGACACGGCCCAGACTC
                      250       260       270       280       290       300

280       290       300       310       320       330
Azospirillum   CTACGGGAGGCAGCAGTGGGGAATATTGGACAATGGGCGCAAGCCTGATCCAGCAATGCC
               ::::::::::::::::::::::::::::::::::::::::::::::::::::::::::::
AF521650       CTACGGGAGGCAGCAGTGGGGAATATTGGACAATGGGCGCAAGCCTGATCCAGCAATGCC
                      310       320       330       340       350       360

340       350       360       370       380       390
Azospirillum   GCGTGAGTGATGAAGGCCTTAGGGTTGTAAAGCTCTTTCGCACGCGACGATGATGACGGT
               ::::::::::::::::::::::::::::::::::::::::::::::::::::::::::::
AF521650       GCGTGAGTGATGAAGGCCTTAGGGTTGTAAAGCTCTTTCGCACGCGACGATGATGACGGT
                      370       380       390       400       410       420

400       410       420       430       440       450
Azospirillum   AGCGTGAGAAGAAGCCCCGGCTAACTTCGTGCCAGCAGCCGCGGTAATACGAAGGGGGCT
               ::::::::::::::::::::::::::::::::::::::::::::::::::::::::::::
AF521650       AGCGTGAGAAGAAGCCCCGGCTAACTTCGTGCCAGCAGCCGCGGTAATACGAAGGGGGCT
                      430       440       450       460       470       480

460       470       480       490       500       510
Azospirillum   AGCGTTGTTCGGAATTACTGGGCGTAAAGGGCGCGTAGGCGGCCTTGTCAGTCAGAAGTG
               :::::::::::::::::::::::::::::::::::::::::::::::  :::::::::::
AF521650       AGCGTTGTTCGGAATTACTGGGCGTAAAGGGCGCGTAGGCGGCCTGTTTAGTCAGAAGTG
                      490       500       510       520       530       540
```

Fig. 1-2

```
              520        530        540        550        560        570
Azospirillum  AAAGCCCCGGGCTCAACCTGGGAACCGCTTTTGATACTGCAAGGCTTGAGTTCCGGAGAG
              ::::::::::::::::::::::::::    ::::::::::::::: ::::::::::::::::::::
AF521650      AAAGCCCCGGGCTCAACCTGGGAATAGCTTTTGATACTGGCAGGCTTGAGTTCCGGAGAG
              550        560        570        580        590        600

580        590        600        610        620        630
Azospirillum  GATGGTGGAATTCCCAGTGTAGAGGTGAAATTCGTAGATATTGGGAAGAACACCGGTGGC
              ::::::::::::::::::::::::::::::::::::::::::::::::::::::::::::
AF521650      GATGGTGGAATTCCCAGTGTAGAGGTGAAATTCGTAGATATTGGGAAGAACACCGGTGGC
              610        620        630        640        650        660

640        650        660        670        680        690
Azospirillum  GAAGGCGGCCATCTGGACGGACACTGACGCTGAGGCGCGAAAGCGTGGGGAGCAAACAGG
              ::::::::::::::::::::::::::::::::::::::::::::::::::::::::::::
AF521650      GAAGGCGGCCATCTGGACGGACACTGACGCTGAGGCGCGAAAGCGTGGGGAGCAAACAGG
              670        680        690        700        710        720

700        710        720        730        740        750
Azospirillum  ATTAGATACCCTGGTAGTCCACGCCGTAAACGATGAATGCTAGACGTCGGGGTGCATGCA
              ::::::::::::::::::::::::::::::::::::::::::::::::::::::::::::
AF521650      ATTAGATACCCTGGTAGTCCACGCCGTAAACGATGAATGCTAGACGTCGGGGTGCATGCA
              730        740        750        760        770        780

760        770        780        790        800        810
Azospirillum  CTTCGGTGTCGCCGCTAACGCATTAAGCATTCCGCCTGGGGAGTACGGCCGCAAGGTTAA
              ::::::::::::::::::::::::::::::::::::::::::::::::::::::::::::
AF521650      CTTCGGTGTCGCCGCTAACGCATTAAGCATTCCGCCTGGGGAGTACGGCCGCAAGGTTAA
              790        800        810        820        830        840

820        830        840        850        860        870
Azospirillum  AACTCAAAGGAATTGACGGGGGCCCGCACAAGCGGTGGAGCATGTGGTTTAATTCGAAGC
              ::::::::::::::::::::::::::::::::::::::::::::::::::::::::::::
AF521650      AACTCAAAGGAATTGACGGGGGCCCGCACAAGCGGTGGAGCATGTGGTTTAATTCGAAGC
              850        860        870        880        890        900

880        890        900        910        920        930
Azospirillum  AACGCGCAGAACCTTACCAACCCCTTGACATGTCCACTATGGGCTTGAGAGATCAGGTCCT
              ::::::::::::::::::::::::::::::::::::::::::::::::::  :::: :::::::::
AF521650      AACGCGCAGAACCTTACCAACCCCTTGACATGTCCACTATGGGCTTCAGAGATGAGGTCCT
              910        920        930        940        950        960

940        950        960        970        980        990
Azospirillum  TCGGTTCGGCCGGGTGGAACACAGGTGCTGCATGGCTGTCGTCAGCTCGTGTCGTGAGAT
              ::::::::::::::::::::::::::::::::::::::::::::::::::::::::::::
AF521650      TCGGTTCGGCCGGGTGGAACACAGGTGCTGCATGGCTGTCGTCAGCTCGTGTCGTGAGAT
              970        980        990        1000       1010       1020

1000       1010       1020       1030       1040       1050
Azospirillum  GTTGGGTTAAGTCCCGCAACGAGCGCAACCCCTACCGTCAGTTGCCATCATTCAGTTGGG
              ::::::::::::::::::::::::::::::::::::::::::::::::::::::::::::
AF521650      GTTGGGTTAAGTCCCGCAACGAGCGCAACCCCTACCGTCAGTTGCCATCATTCAGTTGGG
              1030       1040       1050       1060       1070       1080

1060       1070       1080       1090       1100       1110
Azospirillum  CACTCTGGTGGAACCGCCGGTGACAAGCCGGAGGAAGGCGGGGATGACGTCAAGTCCTCA
              ::::::::::::::::::::::::::::::::::::::::::::::::::::::::::::
AF521650      CACTCTGGTGGAACCGCCGGTGACAAGCCGGAGGAAGGCGGGGATGACGTCAAGTCCTCA
              1090       1100       1110       1120       1130       1140
```

Fig. 1-3

```
                 1120       1130       1140       1150       1160       1170
Azospirillum TGGCCCTTATGGGTTGGGCTACACACGTGCTACAATGGCGGTGACAGTGGGAAGCGAAGT
             ::::::::::::::::::::::::::::::::::::::::::::::::::::  ::::::
AF521650     TGGCCCTTATGGGTTGGGCTACACACGTGCTACAATGGCGGTGACAGTGGGAGGCGAAGT
                 1150       1160       1170       1180       1190       1200

1180       1190       1200       1210       1220       1230
Azospirillum CGCGAGATGGAGCCAATCCCCAAAAGCCGTCTCAGTTCGGATCGTACTCTGCAACTCGAG
             :::::::::::::: ::::::::::::::::::::::::::::  :::::::::::::::
AF521650     CGCGAGATGGAGCAAATCCCCAAAAGCCGTCTCAGTTCGGATTGCACTCTGCAACTCGAG
                 1210       1220       1230       1240       1250       1260

1240       1250       1260       1270       1280       1290
Azospirillum TGCGTGAAGTTGGAATCGCTAGTAATCGCGGATCAGCACGCCGCGGTGAATACGTTCCCG
             :::  :::::::::::::::::::::::::::::::::::::::::::::::::::::::
AF521650     TGCATGAAGTTGGAATCGCTAGTAATCGCGGATCAGCACGCCGCGGTGAATACGTTCCCG
                 1270       1280       1290       1300       1310       1320

1300       1310       1320       1330       1340       1350
Azospirillum GGCCTTGTACACACCGCCCGTCACACCATGGGAGTTGGCTTTACCCGAAGACGGTGCGCT
             ::::::::::::::::::::::::::::::::::::::::::::::::::::::::::::
AF521650     GGCCTTGTACACACCGCCCGTCACACCATGGGAGTTGGCTTTACCCGAAGACGGTGCGCT
                 1330       1340       1350       1360       1370       1380

1360       1370       1380       1390       1400       1410
Azospirillum AACCCGCAAGGGAGGCAGCCGGCCACGGTAAGGTCAGCGACTGGGGTGAAGTCGTAACAA
             ::::  ::::  ::::::::::::::::::::::::::::::::::::::::::::::::
AF521650     AACCGGCAACGGAGGCAGCCGGCCACGGTAAGGTCAGCGACTGGGGTGAAGTCGTAACAA
                 1390       1400       1410       1420       1430       1440

1420
Azospirillum GGTAGCCGTAGGG
             :::::::::::::
AF521650     GGTAGCCGTAGGGGAACCTGCGGCTGGATCACCTCCT
                 1450       1460       1470
```

Fig. 2-1

```
                              10         20         30         40         50
Herbaspirillum        ACGCTGGCGGCATGCCTTACACATGCAAGTCGAACGGCAGCATAGGAGCTTGCTC
                        ::::::::::::::::::::::::::::::::::::::::::::::::::::
AF137508            ATTGAACGCTGGCGGCATGCCTTACACATGCAAGTCGAACGGCAGCATAGGAGCTTGCTC
                       10         20         30         40         50         60

60         70         80         90        100        110
Herbaspirillum        CTGATGGCGAGTGGCGAACGGGTGAGTAATATATCGGAACGTGCCCTAGAGTGGGGGATA
                      ::::::::::::::::::::::::::::::::::::::::::::::::::::::::::::
AF137508              CTGATGGCGAGTGGCGAACGGGTGAGTAATATATCGGAACGTGCCCTAGAGTGGGGGATA
                              70         80         90        100        110        120

120        130        140        150        160        170
Herbaspirillum        ACTAGTCGAAAGACTAGCTAATACCGCATACGATCTAAGGATGAAAGTGGGGGATCGCAA
                      ::::::::::::::::::::::::::::::::::::::::::::::::::::::::::::
AF137508              ACTAGTCGAAAGACTAGCTAATACCGCATACGATCTAAGGATGAAAGTGGGGGATCGCAA
                             130        140        150        160        170        180

180        190        200        210        220        230
Herbaspirillum        GACCTCATGCTCCTGGAGCGGCCGATATCTGATTAGCTAGTTGGTGGGGTAAAAGCCTAC
                      ::::::::::::::::::::::::::::::::::::::::::::::::::::::::::::
AF137508              GACCTCATGCTCCTGGAGCGGCCGATATCTGATTAGCTAGTTGGTGGGGTAAAAGCCTAC
                             190        200        210        220        230        240

240        250        260        270        280        290
Herbaspirillum        CAAGGCGACGATCAGTAGCTGGTCTGAGAGGACGACCAGCCACACTGGGACTGAGACACG
                      ::::::::::::::::::::::::::::::::::::::::::::::::::::::::::::
AF137508              CAAGGCGACGATCAGTAGCTGGTCTGAGAGGACGACCAGCCACACTGGGACTGAGACACG
                             250        260        270        280        290        300

300        310        320        330        340        350
Herbaspirillum        GCCCAGACTCCTACGGGAGGCAGCAGTGGGGAATTTTGGACAATGGGGGCAACCCTGATC
                      ::::::::::::::::::::::::::::::::::::::::::::::::::::::::::::
AF137508              GCCCAGACTCCTACGGGAGGCAGCAGTGGGGAATTTTGGACAATGGGGGCAACCCTGATC
                             310        320        330        340        350        360

360        370        380        390        400        410
Herbaspirillum        CAGCAATGCCGCGTGAGTGAAGAAGGCCTTCGGGTTGTAAAGCTCTTTTGTCAGGGAAGA
                      ::::::::::::::::::::::::::::::::::::::::::::::::::::::::::::
AF137508              CAGCAATGCCGCGTGAGTGAAGAAGGCCTTCGGGTTGTAAAGCTCTTTTGTCAGGGAAGA
                             370        380        390        400        410        420

420        430        440        450        460        470
Herbaspirillum        AACGGTAGTAGCTAATATCTATTACTAATGACGGTACCTGAAGAATAAGCACCGGCTAAC
                      ::::::  ::::::::::::::: :::::::::::::::::::::::::::::::::::::
AF137508              AACGGTGGTAGCTAATATCTACTACTAATGACGGTACCTGAAGAATAAGCACCGGCTAAC
                             430        440        450        460        470        480

480        490        500        510        520        530
Herbaspirillum        TACGTGCCAGCAGCCGCGGTAATACGTAGGGTGCAAGCGTTAATCGGAATTACTGGGCGT
                      ::::::::::::::::::::::::::::::::::::::::::::::::::::::::::::
AF137508              TACGTGCCAGCAGCCGCGGTAATACGTAGGGTGCAAGCGTTAATCGGAATTACTGGGCGT
                             490        500        510        520        530        540
```

Fig. 2-2

```
                540       550       560       570       580       590
Herbaspirillum  AAAGCGTGCGCAGGCGGTTGTGTAAGACAGATGTGAAATCCCCGGGCTCAACCTGGGAAT
                ::::::::::::::::::::::::::::  ::::::::::::::::::::::::::::::
AF137508        AAAGCGTGCGCAGGCGGTTGTGTAAGTCAGATGTGAAATCCCCGGGCTCAACCTGGGAAT
                  550       560       570       580       590       600

600       610       620       630       640       650
Herbaspirillum  TGCATTTGTGACTGCACGGCTAGAGTGTGTCAGAGGGGGGTAGAATTCCACGTGTAGCAG
                ::::::::  ::::::::::::::::::::::::::::::::::::::::::::::::::
AF137508        TGCATTTGAGACTGCACGGCTAGAGTGTGTCAGAGGGGGGTAGAATTCCACGTGTAGCAG
                  610       620       630       640       650       660

660       670       680       690       700       710
Herbaspirillum  TGAAATGCGTAGATATGTGGAGGAATACCGATGGCGAAGGCAGCCCCCTGGGATAACACT
                ::::::::::::::::::::::::::::::::::::::::::::::::::::::::::::
AF137508        TGAAATGCGTAGATATGTGGAGGAATACCGATGGCGAAGGCAGCCCCCTGGGATAACACT
                  670       680       690       700       710       720

720       730       740       750       760       770
Herbaspirillum  GACGCTCATGCACGAAAGCGTGGGGAGCAAACAGGATTAGATACCCTGGTAGTCCACGCC
                ::::::::::::::::::::::::::::::::::::::::::::::::::::::::::::
AF137508        GACGCTCATGCACGAAAGCGTGGGGAGCAAACAGGATTAGATACCCTGGTAGTCCACGCC
                  730       740       750       760       770       780

780       790       800       810       820       830
Herbaspirillum  CTAAACGATGTCTACTAGTTGTCGGGTCTTAATTGACTTGGTAACGCAGCTAACGCGTGA
                ::::::::::::::::::::::::::::::::::::::::::::::::::::::::::::
AF137508        CTAAACGATGTCTACTAGTTGTCGGGTCTTAATTGACTTGGTAACGCAGCTAACGCGTGA
                  790       800       810       820       830       840

840       850       860       870       880       890
Herbaspirillum  AGTAGACCGCCTGGGGAGTACGGTCGCAAGATTAAAACTCAAAGGAATTGACGGGGACCC
                ::::::::::::::::::::::::::::::::::::::::::::::::::::::::::::
AF137508        AGTAGACCGCCTGGGGAGTACGGTCGCAAGATTAAAACTCAAAGGAATTGACGGGGACCC
                  850       860       870       880       890       900

900       910       920       930       940       950
Herbaspirillum  GCACAAGCGGTGGATGATGTGGATTAATTCGATGCAACGCGAAAAACCTTACCTACCCTT
                ::::::::::::::::::::::::::::::::::::::::::::::::::::::::::::
AF137508        GCACAAGCGGTGGATGATGTGGATTAATTCGATGCAACGCGAAAAACCTTACCTACCCTT
                  910       920       930       940       950       960

960       970       980       990       1000      1010
Herbaspirillum  GACATGGTCGGAATCCTGAAGAGATTTAGGAGTGCTCGAAAGAGAACCGGCGCACAGGTG
                :::::::::::::::::::::::::::: :::::::::::::::::::::::::::::::
AF137508        GACATGGTCGGAATCCTGAAGAGATTTGGGAGTGCTCGAAAGAGAACCGGCGCACAGGTG
                  970       980       990       1000      1010      1020

1020      1030      1040      1050      1060      1070
Herbaspirillum  CTGCATGGCTGTCGTCAGCTCGTGTCGTGAGATGTTGGGTTAAGTCCCGCAACGAGCGCA
                ::::::::::::::::::::::::::::::::::::::::::::::::::::::::::::
AF137508        CTGCATGGCTGTCGTCAGCTCGTGTCGTGAGATGTTGGGTTAAGTCCCGCAACGAGCGCA
                  1030      1040      1050      1060      1070      1080

1080      1090      1100      1110      1120      1130
Herbaspirillum  ACCCTTGTCATTAGTTGCTACGAAAGGGCACTCTAATGAGACTGCCGGTGACAAACCGGA
                ::::::::::::::::::::::::::::::::::::::::::::::::::::::::::::
AF137508        ACCCTTGTCATTAGTTGCTACGAAAGGGCACTCTAATGAGACTGCCGGTGACAAACCGGA
                  1090      1100      1110      1120      1130      1140
```

Fig. 2-3

```
                      1140      1150      1160      1170      1180      1190
Herbaspirillum  GGAAGGTGGGGATGACGTCAAGTCCTCATGGCCCTTATGGGTAGGGCTTCACACGTCATA
                ::::::::::::::::::::::::::::::::::::::::::::::::::::::::::::
AF137508        GGAAGGTGGGGATGACGTCAAGTCCTCATGGCCCTTATGGGTAGGGCTTCACACGTCATA
                      1150      1160      1170      1180      1190      1200

1200      1210      1220      1230      1240      1250
Herbaspirillum  CAATGGTACATACAGAGGGCCGCCAACCCGCGAGGGGGAGCTAATCCCAGAAAGTGTATC
                ::::::::::::::::::::::::::::::::::::::::::::::::::::::::::::
AF137508        CAATGGTACATACAGAGGGCCGCCAACCCGCGAGGGGGAGCTAATCCCAGAAAGTGTATC
                      1210      1220      1230      1240      1250      1260

1260      1270      1280      1290      1300      1310
Herbaspirillum  GTAGTCCGGATTGTAGTCTGCAACTCGACTACATGAAGTTGGAATCGCTAGTAATCGCGG
                ::::::::::::::::::::::::::::::::::::::::::::::::::::::::::::
AF137508        GTAGTCCGGATTGTAGTCTGCAACTCGACTACATGAAGTTGGAATCGCTAGTAATCGCGG
                      1270      1280      1290      1300      1310      1320

1320      1330      1340      1350      1360      1370
Herbaspirillum  ATCAGCATGTCGCGGTGAATACGTTCCCGGGTCTTGTACACACCGCCCGTCACACCATGG
                ::::::::::::::::::::::::::::::::::::::::::::::::::::::::::::
AF137508        ATCAGCATGTCGCGGTGAATACGTTCCCGGGTCTTGTACACACCGCCCGTCACACCATGG
                      1330      1340      1350      1360      1370      1380

1380      1390      1400      1410      1420      1430
Herbaspirillum  GAGCGGGTTTTACCAGAAGTGGGTAGCCTAACCGCAAGGAGGGCGCTCACCACGGTAGGA
                ::::::::::::::::::::::::::::::::::::::::::::::::::::::::::::
AF137508        GAGCGGGTTTTACCAGAAGTGGGTAGCCTAACCGCAAGGAGGGCGCTCACCACGGTAGGA
                      1390      1400      1410      1420      1430      1440

1440      1450      1460      1470
Herbaspirillum  TTCGTGACTGGGGTGAAGTCGTAACAAGG-AGCCGTATCGGAA
                ::::::::::::::::::::::::::::: :::::::::::::
AF137508        TTCGTGACTGGGGTGAAGTCGTAACAAGGTAGCCGTATCGGAAGG
                      1450      1460      1470      1480
```

Control   Azospirillum   Azospirillum   Azospirillum
              $10^8$          $10^7$          $10^6$ Day 10

Day 15

Control    Azospirillum    Herbaspirillum

BACTERIA AND METHOD FOR CONTROLLING PLANT DISEASE USING THE SAME

TECHNICAL FIELD

The present invention relates to novel bacterial endophytes, a method for controlling pathogenic fungal, pathogenic bacterial, or pathogenic viral disease in plants using the novel bacterial endophytes, and plants produced by such method.

BACKGROUND ART

Conventional pest control technology based on the use of agricultural chemicals has contributed to efficient food security. However, recently, environmentally-sound agriculture using no agricultural chemicals or reduced amounts of agricultural chemicals and satisfying not only cultivation efficiency but also reassurance and safety is desired. Furthermore, pest control technology (e.g., microbial pesticides) fulfilling such demand has also become necessary.

DISCLOSURE OF THE INVENTION

An object of the present invention is to provide a means for imparting resistance against pathogenic fungal, pathogenic bacterial, or pathogenic viral disease to agriculturally useful plants.

The present invention encompasses the following (1) to (9).
(1) A method for controlling pathogenic fungal, pathogenic bacterial, or pathogenic viral disease in a plant, comprising a step of artificially infecting a plant with a bacterium belonging to the genus *Azospirillum* or the genus *Herbaspirillum* capable of imparting resistance against pathogenic fungal, pathogenic bacterial, or pathogenic viral disease to the host plant by living symbiotically within the plant.
(2) The method according to (1), in which the bacterium is at least one member selected from the group consisting of a novel bacterium belonging to the genus *Azospirillum* (accession No. NITE BP-194), a novel bacterium belonging to the genus *Herbaspirillum* (accession No. NITE BP-193), and a bacterium of a mutant strain thereof.
(3) The method according to (1) or (2), in which the plant belongs to the family Gramineae or the family Brassicaceae.
(4) The method according to any one of (1) to (3), in which the bacterium is caused to infect a plant during the period in which seedlings are raised.
(5) A disease control agent for controlling pathogenic fungal, pathogenic bacterial, or pathogenic viral disease in a plant, containing as an active ingredient a bacterium belonging to the genus *Azospirillum* or the genus *Herbaspirillum* capable of imparting resistance against pathogenic fungal, pathogenic bacterial, or pathogenic viral disease to a host plant by living symbiotically within the plant.
(6) The control agent according to (5), in which the bacterium is at least one member selected from the group consisting of a novel bacterium belonging to the genus *Azospirillum* (accession No. NITE BP-194), a novel bacterium belonging to the genus *Herbaspirillum* (accession No. NITE BP-193), and a bacterium of a mutant strain thereof.
(7) A novel bacterial strain belonging to the genus *Azospirillum* (accession No. NITE BP-194) or a mutant strain thereof capable of imparting resistance against pathogenic fungal, pathogenic bacterial, or pathogenic viral disease to a host plant by living symbiotically within the plant.
(8) A novel bacterial strain belonging to the genus *Herbaspirillum* (accession No. NITE BP-193) or a mutant strain thereof capable of imparting resistance against pathogenic fungal, pathogenic bacterial, or pathogenic viral disease to a host plant by living symbiotically within the plant.
(9) A plant having resistance against pathogenic fungal, pathogenic bacterial, or pathogenic viral disease, which is artificially infected with at least one member selected from the group consisting of a novel bacterial strain belonging to the genus *Azospirillum* (accession No. NITE BP-194), a novel bacterial strain belonging to the genus *Herbaspirillum* (accession No. NITE BP-193), and a mutant strain thereof capable of imparting resistance against pathogenic fungal, pathogenic bacterial, or pathogenic viral disease to a host plant by living symbiotically within the plant.

In this description, the term "novel bacterium belonging to the genus *Azospirillum*" refers to a bacterium belonging to the genus *Azospirillum*, which was isolated and identified in Example 1 and deposited under accession No. NITE BP-194.

In this description, the term "novel bacterium belonging to the genus *Herbaspirillum*" refers to a bacterium belonging to the genus *Herbaspirillum*, which was isolated and identified in Example 2 and deposited under accession No. NITE BP-193.

This description includes part or all of the contents as disclosed in the description and/or drawings of Japanese Patent Application No. 2006-58483, which is priority document of the present application.

BRIEF DESCRIPTION OF THE DRAWINGS

FIG. 1-1 shows the result of comparing the novel bacterium belonging to the genus *Azospirillum* with the *Azospirillum* sp. Arm2-2 strain (Accession No. AF521650) in terms of 16S rDNA (continued to FIG. 1-2).

FIG. 1-2 shows the result of comparing the novel bacterium belonging to the genus *Azospirillum* with the *Azospirillum* sp. Arm2-2 strain (Accession No. AF521650) in terms of 16S rDNA (continued to FIG. 1-3).

FIG. 1-3 shows the result of comparing the novel bacterium belonging to the genus *Azospirillum* with the *Azospirillum* sp. Arm2-2 strain (Accession No. AF521650) in terms of 16S rDNA.

FIG. 2-1 shows the result of comparing the novel bacterium belonging to the genus *Herbaspirillum* with *Herbaspirillum rubrisubalbicans* (Accession No. AF137508) in terms of 16S rDNA (continued to FIG. 2-2).

FIG. 2-2 shows the result of comparing the novel bacterium belonging to the genus *Herbaspirillum* with *Herbaspirillum rubrisubalbicans* (Accession No. AF137508) in terms of 16S rDNA (continued to FIG. 2-3).

FIG. 2-3 shows the result of comparing the novel bacterium belonging to the genus *Herbaspirillum* with *Herbaspirillum rubrisubalbicans* (Accession No. AF137508) in terms of 16S rDNA.

FIG. 3 shows the positional relationship between the ITS region and nested PCR primers.

PREFERRED EMBODIMENTS OF THE INVENTION

Figure 3:
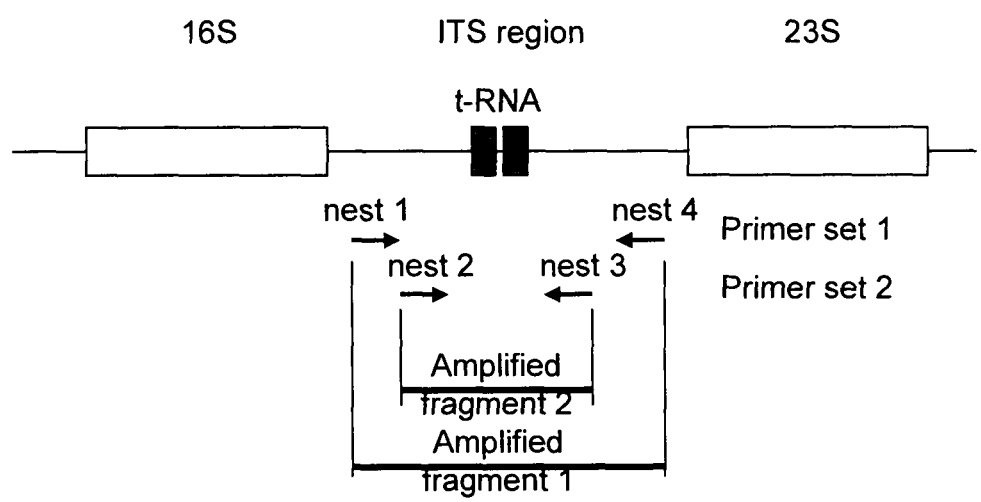

Examples of plants to which resistance against pathogenic fungal, pathogenic bacterial, or pathogenic viral disease is imparted through infection with the bacteria of the present invention include plants of the family Gramineae or plants of the family Brassicaceae. Examples of the plants of the family Gramineae include, particularly, cereals such as rice, wheat, barley, rye, triticale, Coix lacryma-joli, Sorghum, oat, maize, sugarcane, foxtail millet, and Japanese millet. Further examples of the plants of the family Gramineae include forages or herbages such as Zoysia, buffalo grass, Bermuda grass, weeping grass, centipede grass, carpet grass, dallies grass, kikuyu grass, and Saint Augustine grass. Examples of the plants of the family Brassicaceae include particularly, rapeseed, turnip, qing-geng-cai, nozawana (*Brassica rapa* var. *hakabura*), Indian mustard, takana (*Brassica juncea* var. *integlifolia*), kobutakana (*Brassica juncea* var. *integlifolia*), mizuna (*Brassica rapa* var. *laciniifolia*), Kohlrabi, arugula, cress, Chinese flat cabbage, cauliflower, cabbage, kale, Chinese cabbage, komatsuna (*Brassica chinensis*), radish, radioxenon, broccoli, brussels sprouts, Wasabia, and horseradish.

The present invention further relates to the above plants which have been artificially infected with the bacteria of the present invention so as to have resistance against pathogenic fungal, pathogenic bacterial, or pathogenic viral disease.

Examples of plant diseases caused by pathogenic fungi, which can be controlled according to the present invention, include rice blast (pathogenic fungus: *Magnaporthe grisea*), Helminthosporium leaf spot of rice (pathogenic fungus: *Bipolaris leersiae*), bakanae disease of rice (pathogenic fungus: *Gibberella fujikuroi*), sheath blight disease of rice (pathogenic fungus: *Thanatephorus cucumuris*), yellow dwarf disease of rice (pathogenic fungus: *Ssclerophthora macrospora*), pseudo-sheath blight disease of rice (pathogenic fungus: *Rhizoctonia solani*), ergot disease of wheat (pathogenic fungus: *Claviceps purpurea*), loose kernel smut of wheat (pathogenic fungus: *Ustilago tritici*), loose kernel smut in barley (pathogenic fungus: *Ustilago nuda*), Typhula snow blight of rye (pathogenic fungus: *Typhula incarnata*), spot blotch of rye (pathogenic fungus: *Cochliobolus sativus*), take-all of rice, oat, wheat, barley, and rye (pathogenic fungus: *Gaeumannomyces graminis*), maize leaf blight (pathogenic fungus: *Setosphaeria turcica*), clubroot of vegetables such as plants of the family Brassicaceae (pathogenic fungus: *Plamodiophora brassicae*), damping-off of vegetables such as plants of the family Brassicaceae (pathogenic fungus: *Thanatephorus cucumeris*), Chinese cabbage yellowing disease (pathogenic fungus: *Verticillium albo-atrum*), radish yellows (pathogenic fungus: *Fusarium oxysporum* f. sp. *Raphani*), white rust of radish (pathogenic fungus: *Albugo macrospora*), and white rust of komatsuna (*Brassica chinensis*) (pathogenic fungus: *Albugo macrospora*).

Examples of plant diseases caused by pathogenic bacteria, which can be controlled according to the present invention, include bacterial leaf blight of rice (pathogenic bacterium: *Xanthonmonas oryzae* pv. *oryzae*), bacterial grain rot of rice (pathogenic bacterium: *Pseudomonas glumae*), soft rot of vegetables that cause severe damages on Chinese cabbage, plants of the family Brassicaceae, and the like (pathogenic bacterium: *Erwinia carotovora*), and black rot of cabbage (*Xanthomonas campestris* pv. *campestris*).

Examples disclosed in this description demonstrate that the bacteria according to the present invention are effective for controlling plant diseases caused by pathogenic fungi and plant diseases caused by pathogenic bacteria. This shows that the bacteria according to the present invention enhance the host plants' own disease resistance. Therefore, the bacteria according to the present invention are effective not only for controlling plant diseases caused by pathogenic fungi or pathogenic bacteria, but also for controlling plant diseases caused by pathogenic fungi, pathogenic bacteria, or pathogenic viruses.

Examples of plant diseases caused by pathogenic viruses, which can be controlled according to the present invention, include rice dwarf (rice dwarf reovirus), rice stripe (rice stripe tenuivirus), rice black-streaked dwarf (rice black-streaked dwarf reovirus), rice necrosis mosaic (rice necrosis mosaic potyvirus), rice waika (rice waika virus), wheat yellow mosaic (wheat yellow mosaic virus), barley yellow mosaic (barley yellow mosaic virus), barley stripe mosaic (Barley stripe hordeivirus), and viral diseases of radish, turnip, and komatsuna (*Brassica chinensis*) such as diseases caused by cucumber mosaic virus, turnip mosaic potivirus, radish enation mosaic comovirus, and broad bean wilt fabavirus.

Bacteria that can be used for the present invention are not particularly limited, as long as they are bacteria belonging to the genus *Azospirillum* or the genus *Herbaspirillum* capable of imparting resistance against pathogenic fungal, pathogenic bacterial, or pathogenic viral disease to host plants by living symbiotically within the plants. Specific examples of such bacteria include a novel bacterium belonging to the genus *Azospirillum* (accession No. NITE BP-194) and a novel bacterium belonging to the genus *Herbaspirillum* (accession No. NITE BP-193). Further examples of the same include, but are not limited to, bacteria having ability equivalent to that of the novel bacterium belonging to the genus *Azospirillum* (accession No. NITE BP-194) or the novel bacterium belonging to the genus *Herbaspirillum* (accession No. NITE BP-193), such as a bacterium belonging to the genus *Azospirillum* having the same ability of assimilating carbon sources as that of the novel bacterium belonging to the genus *Azospirillum* described in Example 1, a bacterium belonging the genus *Azospirillum* having 16S rDNA that contains the nucleotide sequence shown in SEQ ID NO: 1 as at least a portion, a bacterium belonging to the genus *Herbaspirillum* having the same ability of assimilating carbon sources as that of the novel bacterium belonging to the genus *Herbaspirillum* described in Example 2, and a bacterium belonging to the genus *Herbaspirillum* having 16S rDNA that contains the nucleotide sequence shown in SEQ ID NO: 2 as at least a portion. Furthermore, a mutant strain that is produced by subjecting the novel bacterium belonging to the genus *Azospirillum* (accession No. NITE BP-194) or the novel bacterium belonging to the genus *Herbaspirillum* (accession No. NITE BP-193) to mutagenesis and is capable of imparting resistance against pathogenic fungal, pathogenic bacterial, or pathogenic viral disease to host plants by living symbiotically within the plants can be adequately used in the present invention. Preferable examples of such mutant strains include a bacterium belonging to the genus *Azospirillum* and having the same ability of assimilating carbon sources as that of the novel bacterium belonging to the genus *Azospirillum* described in Example 1, a bacterium belonging to the genus *Azospirillum* and having 16S rDNA that contains the nucleotide sequence shown in SEQ ID NO. 1 as at least a portion, a bacterium belonging to the genus *Herbaspirillum* and having the same ability of assimilating carbon sources as that of the novel bacterium belonging to the genus *Herbaspirillum* described in Example 2, and a bacterium belonging to the genus *Herbaspirillum* and having 16S rDNA that contains the nucleotide sequence shown in SEQ ID NO: 2 as at least a portion. Mutagenesis can be carried out by using any appropriate mutagen. Here, the term "mutagen" is broadly interpreted, so that the term should be understood as referring not only to agents having mutagenic effects, but also to treatment having mutagenic effects such as UV irradiation. Examples of adequate mutagens include ethylmethane sulfonate, UV irradiation, N-methyl-N'-nitro-N-nitrosoguanidine, a nucleotide base analogue such as bromouracil, and acridines. Furthermore, any other effective mutagen can also be used herein.

Bacteria to be used in the present invention can be cultured under general conditions by a general culture method such as shake culture. Examples of media to be used for culturing include synthetic or natural media each containing saccharides such as glucose, sucrose, starch, and dextrin as carbon sources, ammonium salts such as ammonium sulfate, ammonium chloride, and ammonium nitrate as nitrogen sources, and nitrate as inorganic nitrogen sources, or yeast extract, corn steep liquor, meat extract, wheat germ, polypeptone, cane trash (bagasse), brewer grain, soy flour, rice bran, and fish meal as organic nitrogen sources, and salts containing phosphorus, potassium, manganese, magnesium, iron, or the like (e.g., potassium primary phosphate, magnesium sulfate, manganese sulfate, and ferrous sulfate) as inorganic salts.

The present invention further relates to a disease control agent for controlling pathogenic fungal, pathogenic bacterial, or pathogenic viral disease in plants, comprising as an active ingredient the bacteria of the present invention. As such plant disease control agent, the culture solution of the bacterium of the present invention can be used intact. Furthermore, products with high concentrations of the bacteria of the present invention prepared by separating the bacterial culture solutions via a method such as membrane separation, centrifugation, or separation via filtration can also be used herein.

Furthermore, products prepared by drying the culture solutions of the bacteria of present invention can also be used as the plant disease control agents of the present invention. Moreover, products prepared by adsorbing the culture solutions of the bacteria of the present invention to porous adsorbing materials such as activated carbon powder, diatomaceous earth, or talc and then drying the resultants can also be used herein. A method for drying such product may be a general method, such as freeze drying or vacuum drying. Such dried product can be further pulverized by a pulverization means such as ball mill after drying.

The bacteria of the present invention can further be used individually as they are in the present invention in the forms of the above-mentioned culture solutions, products with high bacterial concentrations, or dried products. Furthermore, the bacteria of the present invention can be formulated into forms similar to those of general microbial preparations (e.g., powders, wettable powders, emulsions, solutions, flowable agents, or coating agents) in combination with any other arbitrary ingredients and then provided as compositions for plant disease control. Examples of such arbitrary ingredients that can be used in combination include materials acceptable for application to plants, such as solid carriers or auxiliary materials.

The bacteria of the present invention are preferably caused to infect plants during the vegetative growth period of the plants.

Examples of possible methods for applying the bacteria of the present invention or compositions containing such bacteria to plants include spraying, affusion, dipping (dobu-zuke), coating of plants with such bacteria or compositions, bringing such bacteria or compositions into contact with artificially provided incisions, injection with the use of a syringe, mixing into soil, mixing into water culture medium, and mixing of such bacteria or compositions with sand or the like followed by spraying (e.g., sandblasting). When a suspension prepared by suspending a bacterium of the present invention is applied to plants via affusion, the concentration of the bacterium of the present invention in such suspension preferably ranges from $10^4$ to $10^{12}$ CFU/ml.

Example 1

Isolation and Identification of the Novel Bacterium Belonging to the Genus *Azospirillum*

Stems of cultivated Nipponbare rice (*Oryza sativa* cv. Nipponbare) with a length of approximately 3 cm were collected and then subjected to surface sterilization using 70% ethanol and a 1% sodium hypochlorite solution. The product was ground down with a sterilized mortar while adding sterilized 0.85% sodium chloride water and sea sand. Rennie medium in which nitrogen fixing microbes can exert their nitrogen-fixing activity is known (Rennie, R. J. 1981. Can. J. Micribiol. 27: 8-14). Rennie semisolid medium in test tubes was inoculated with the supernatant of the solution obtained via grinding and then cultured. Nutrient agar medium was inoculated with products in test tubes found to have acetylene-reducing activity, so that single colonies were isolated.

Cultivated rice was inoculated with strains of the thus isolated single colonies and then a test for evaluating resistance against rice blast was conducted. As a result, a bacterial strain capable of imparting disease resistance to rice was selected.

The strain was cultured using nutrient broth, and then genomic DNA was isolated from the microbial cells. With the use of the thus isolated DNA as a template, almost the full-length nucleotide sequence of the 16S rDNA region was determined by a dye-primer method (SEQ ID NO: 1). Homology search was performed between the thus determined nucleotide sequence and the DDBJ/EMBL/GenBank international nucleotide sequence database using the FASTA homology search program.

This strain shared 98.5% homology with the *Azospirillum* sp. Arm2-2 strain (Accession No. AF521650) (FIG. 1). The 16S rDNA of the strain did not match any 16S rDNAs of existing species.

When the substrate assimilability of the strain was examined, the results shown in Table 1 were confirmed.

TABLE 1

Substrates confirmed to be assimilable by the strain selected in Example 1

Glycerol
L-arabinose
Ribose
D-xylose
Galactose
Glucose (anaerobic conditions)
Fructose (anaerobic conditions)
Inositol
Mannitol
Sorbitol
Esculin
D-mannose
N-acetyl-D-glucosamine
Potassium gluconate
n-capric acid
DL-malic acid
Sodium citrate Substrates confirmed to be not assimilable by the strain selected in Example 1

Erythritol
D-arabinose
L-xylose

TABLE 1-continued

Adonitol
β-methyl-D-xylose
Mannose
Sorbose
Rhamnose
Dulcitol
α-methyl-D-mannose
α-methyl-D-glucose
N-acetylglucosamine
Amygdalin
Arbutin
Salicin
Cellobiose
Maltose
Lactose
Melibiose
Saccharose
Trehalose
Inulin
Melezitose
Raffinose
Starch
Glycogen
Xylitol
Gentiobiose
D-turanose
D-lyxose
D-tagatose
D-fucose
L-fucose
D-arabitol
L-arabitol
Gluconate
2-ketogluconic acid
5-ketogluconic acid
Adipic acid
Phenyl acetate Based on the above results, it was concluded that the thus selected strain was the novel bacterial strain belonging to the genus *Azospirillum*.

The present inventors deposited the novel bacterium belonging to the genus *Azospirillum* at the NITE (National Institute of Technology and Evaluation) Patent Microorganisms Depositary (NPMD) (2-5-8, Kazusa-kamatari, Kisarazu-shi, Chiba, Japan) on Feb. 10, 2006, under accession No. NITE BP-194.

Example 2

Isolation and Identification of the Novel Bacterium Belonging to the Genus *Herbaspirillum*

Leaf blades of wild rice (*Oryza barthii* W1407) conserved in Japan, having a length of approximately 3 cm, were collected and then subjected to surface sterilization using 70% ethanol and a 1% sodium hypochlorite solution. The product was ground down with a sterilized mortar while adding sterilized 0.85% sodium chloride water and sea sand. Rennie medium in which nitrogen fixing microbes can exert their nitrogen-fixing activity therein is known (Rennie, R. J. 1981. Can. J. Micribiol. 27: 8-14). Rennie semisolid medium in test tubes was inoculated with the supernatant of the solution obtained via grinding and then cultured. Nutrient agar medium was inoculated with products in test tubes found to have acetylene-reducing activity, so that single colonies were isolated.

Cultivated rice was inoculated with strains of the thus isolated single colonies and then a test for evaluating resistance against rice blast was conducted. As a result, a bacterial strain capable of imparting disease resistance to rice was selected.

The strain was cultured using nutrient broth and then genomic DNA was isolated from the microbial cells. With the use of the thus isolated DNA as a template, almost the full-length nucleotide sequence of the 16S rDNA region was determined by a dye-primer method (SEQ ID NO: 2). Homology search was performed between the thus determined nucleotide sequence and the DDBJ/EMBL/GenBank international nucleotide sequence database using the FASTA homology search program.

This strain shared 99.6% homology with the *Herbaspirillum rubrisubalbicans* (Accession No. AF137508) (FIG. 2). The 16S rDNA of the strain did not match any 16S rDNAs of existing species.

The substrate assimilability of the strain was examined. The strain was compared with the *Herbaspirillum rubrisubalbicans* ATCC19308 strain (having high homology as revealed by homology search of the 16S rDNA nucleotide sequence) in terms of substrate assimilability. The results of the comparison are shown in Table 2. In Table 2, "○" indicates that a substrate was assimilable and "x" indicates that a substrate was not assimilable.

TABLE 2

Comparison of substrate assimilability between the strain selected in Example 2 and the *Herbaspirillum rubrisubalbicans* ATCC19308 strain

| Substrate | Strain selected in Example 2 | *Herbaspirillum rubrisubalbicans* (ATCC 19308) |
| --- | --- | --- |
| N-acetyl-D-glucosamine | x | x |
| L-arabinose | x | ○ |
| α-D-glucose | x | ○ |
| m-inositol | x | x |
| Maltose | x | x |
| D-mannitol | x | ○ |
| D-mannose | x | ○ |
| L-rhamnose | ○ | x |
| Sucrose | x | x |
| Citric acid | x | ○ |

The thus selected strain was found to be capable of assimilating sodium ketoglutarate, m-erythritol, and diammonium sebacate in addition to L-rhamnose.

The thus selected strain was unable to assimilate potassium gluconate, n-capric acid, adipic acid, DL-malic acid, sodium citrate, phenyl acetate, and saccharose in addition to the substrates listed in Table 2.

Based on the above results, it was concluded that the thus selected strain was a novel bacterial strain belonging to the genus *Herbaspirillum*.

The present inventors deposited the novel bacterium belonging to the genus *Herbaspirillum* at the NITE (National Institute of Technology and Evaluation) Patent Microorganisms Depositary (NPMD) (2-5-8, Kazusa-kamatari, Kisarazu-shi, Chiba, Japan) on Feb. 10, 2006, under accession No. NITE BP-193.

Example 3

Detection of the Novel Bacterium Belonging to the Genus *Azospirillum* and the Novel Bacterium Belonging to the Genus *Herbaspirillum* Using a Nested-PCR Method A method for detecting the presence or the absence of infection with the novel bacterium belonging to the genus Azospirillum or the novel bacterium belonging to the genus Herbaspirillum was examined using plants (for which infection with such bacteria had been unknown). As a result, the nested-PCR method was revealed to be effective, as described below.

The nucleotide sequence of the ITS region between 16SrDNA and 23SrDNA of the novel bacterium belonging to the genus Azospirillum and the same of the novel bacterium belonging to the genus Herbaspirillum were determined. The nucleotide sequence of the ITS region of the novel bacterium belonging to the genus Azospirillum is shown in SEQ ID NO: 3 and the same of the novel bacterium belonging to the genus Herbaspirillum is shown in SEQ ID NO: 4.

The nucleotide sequence of the ITS region of each strain was compared with the nucleotide sequences of the ITS regions of related or distantly related 6 to 7 bacterial species registered in the DDBJ/EMBL/GeneBank international nucleotide sequence database using a multiple alignment program ClastalW. Thus, 2 primers sets for amplification of the ITS region were prepared with the use of regions having low homology with those of other bacteria (FIG. 3, Table 3).

Portions in the vicinity of the meristems of plants inoculated with the novel bacterium belonging to the genus Azospirillum or plants inoculated with the novel bacterium belonging to the genus Herbaspirillum were collected. Physiological saline was added to the collected portions and then the resultants were crushed as finely as possible with the use of a mortar or a cell crushing apparatus using beads. DNA was extracted from the solution obtained via crushing. PCR ($1^{st}$ PCR) was performed using a DNA solution as a template and the primer set 1 under conditions shown in Tables 4 and 5. Next, PCR ($2^{nd}$ PCR) was performed using the PCR solution as a template and a inside primer set 2. Thus, detection of target DNA fragments was examined.

In the plants inoculated with the novel bacterium belonging to the genus Azospirillum, the PCR-amplified fragment size obtained using primer set 1 was 484 bp. The PCR-amplified fragment size obtained using primer set 2 was 298 bp. In the plants inoculated with the novel bacterium belonging to the genus Herbaspirillum, the PCR-amplified fragment size obtained using primer set 1 was 356 bp and the PCR-amplified fragment size obtained using primer set 2 was 241 bp.

The above results revealed that: when the amplified fragments with the above sizes were obtained by subjecting samples obtained from subject plants to the nested-PCR method using the primer sets listed in Table 3, it could be concluded that the plants had been infected with the endophyte (the novel bacterium belonging to the genus Azospirillum or the novel bacterium belonging to the genus Herbaspirillum) corresponding to the amplified fragment size.

TABLE 3

PCR primers

| | | Nucleotide sequence | Tm | Length |
|---|---|---|---|---|
| Azospirillum | nest 1 | 5'-TTGAGGGTCCGGCATCAG-3' | 67.45 | 18 |
| | nest 2 | 5'-TCAGGAAGTCCGTATGGCGTT-3' | 67.65 | 21 |
| | nest 3 | 5'-CGTCCCTCGACACCAGCAC-3' | 69.52 | 19 |
| | nest 4 | 5'-GTCGCCTTGTGGGCTTGC-3' | 69.35 | 18 |
| Herbaspirillum | nest 1 | 5'-GCGGTCCGTGACACAA-3' | 63.34 | 16 |
| | nest 2 | 5'-CAAGGTCACTGACTGGCTACTG-3' | 63.76 | 22 |
| | nest 3 | 5'-CACTACGTCTTGCGTTTTGTG-3' | 63.20 | 21 |
| | nest 4 | 5'-CGCAAGAACCGAAGTCCT-3' | 62.99 | 18 |

TABLE 4

$1^{st}$ PCR conditions for the novel bacterium belonging to the genus Azospirillum

| Temperature (° C.) | Time (second) | Number of cycles |
|---|---|---|
| 49 | 30 | 1 |
| 94 | 30 | 40 |
| 68 | 30 | |
| 72 | 15 | |
| 16 | ∞ | |

$2^{nd}$ PCR conditions for the novel bacterium belonging to the genus Azospirillum

| Temperature (° C.) | Time (second) | Number of cycles |
|---|---|---|
| 94 | 10 | 1 |
| 94 | 10 | 40 |
| 69 | 10 | |
| 72 | 10 | |
| 16 | ∞ | |

TABLE 5

1st PCR conditions for the novel bacterium belonging
to the genus *Herbaspirillum*

| Temperature (° C.) | Time (second) | Number of cycles |
|---|---|---|
| 94 | 30 | 1 |
| 94 | 30 | 40 |
| 66 | 20 | |
| 72 | 12 | |
| 16 | ∞ | |

2nd PCR conditions for the novel bacterium belonging
to the genus *Herbaspirillum*

| Temperature (° C.) | Time (second) | Number of cycles |
|---|---|---|
| 94 | 10 | 1 |
| 94 | 10 | 40 |
| 66 | 10 | |
| 72 | 8 | |
| 16 | ∞ | |

Example 4

Detection of the Novel Bacterium Belonging to the Genus *Azospirillum* and the Novel Bacterium Belonging to the Genus *Herbaspirillum* Using the ELISA Method In addition to the method examined in Example 3, a method for detecting the presence or the absence of infection with the novel bacterium belonging to the genus *Azospirillum* or the novel bacterium belonging to the genus *Herbaspirillum* was examined using plants for which infection with such bacteria had been unknown. As a result, the ELISA method was revealed to be effective, as described below.

Polyclonal antibodies against the novel bacterium belonging to the genus *Azospirillum* and the novel bacterium belonging to the genus *Herbaspirillum* were prepared by the following method for the ELISA method. The novel bacterium belonging to the genus *Azospirillum* and the novel bacterium belonging to the genus *Herbaspirillum* were treated with formalin and then solutions of antigen microbes were prepared. Rabbits were each immunized via the back portion with 3 to $4 \times 10^8$ cells. Regarding emulsion preparation, Freund's complete adjuvant was used in the first immunization and Freund's incomplete adjuvant was used from the $2^{nd}$ and the following immunizations. Immunization was performed at intervals of 2 weeks. Whole blood was collected after the $6^{th}$ immunization, thereby preparing a rabbit anti-novel bacterium belonging to the genus *Azospirillum* serum and a rabbit anti-novel bacterium belonging to the genus *Herbaspirillum* serum.

Physiological saline was added to plants inoculated with the novel bacterium belonging to the genus *Azospirillum* or the novel bacterium belonging to the genus *Herbaspirillum* and then the resultants were crushed as finely as possible with the use of a mortar or a cell crushing apparatus using beads. The solution obtained via crushing was weakly centrifuged, large plant residue was removed, and then the solution was subjected to a standard ELISA method using the above polyclonal antibody.

The plant-crushed solution was injected onto a microtiter plate and then bacterial cells were adsorbed to the walls. After washing, the above polyclonal antibody diluted 100,000 fold was caused to react with the product. Solutions obtained via crushing of an uninoculated plant and a known amount of bacterial cells were tested as controls simultaneously. After washing, a peroxidase-labeled secondary antibody (anti-rabbit antibody) was caused to react with the products and then absorbances were measured after chromogenic reactions with the use of peroxidase.

As a result, absorbance levels were more increased in plant samples inoculated with the novel bacterium belonging to the genus *Azospirillum* or the novel bacterium belonging to the genus *Herbaspirillum* than in uninoculated plant samples. Thus, it was revealed that infection with the bacterium used for inoculation (the novel bacterium belonging to the genus *Azospirillum* or the novel bacterium belonging to the genus *Herbaspirillum*) could be concluded. Moreover, the numbers of bacteria that had colonized in plants could be inferred via comparison with the controls.

Example 5

Effects of the Novel Bacterium Belonging to the Genus *Azospirillum* and the Novel Bacterium Belonging to the Genus *Herbaspirillum* to Induce Disease Resistance Against Rice Blast in Rice (Purpose)
In this example, the effects of inducing disease resistance against rice blast (*Magnaporthe grisea* race 007) were verified using rice (*Oryza sativa* Nipponbare) infected with the novel bacterium belonging to the genus *Azospirillum* or the novel bacterium belonging to the genus *Herbaspirillum* (hereinafter, both strains may be referred to with the general term "endophyte"). Rice is a monocotyledonous model plant.
(Experimental Method)
1. Rice plants in the 3-leaf stage were transplanted from cell sheets (5 rice seedlings per 2 cm×2 cm block) to 1% fertilizer solutions for hydroponic cultivation. Rice plants that had grown to reach the 3.5-leaf stage were subjected to affusion using 2 types of solution (prepared with endophyte), so that the concentration ranged from $10^5$ to $10^9$ CFU/ml. On day 5 after treatment with the endophytes, spray-inoculation with a spore suspension (supplemented with 0.2% Tween 20) of blast fungi was performed. The resultants were allowed to stand under dark and in conditions of 100% humidity for 24 hours, followed by 4 days of cultivation in a greenhouse at 25° C. with 60% humidity. On day 5 after inoculation with blast fungi, the numbers of blast lesions that had appeared on leaves of rice plants that had grown to reach the 4-leaf stage were determined. The numbers of lesions in treatment blocks were compared with each other, so that rice blast resistance in each block was evaluated.

2. With the use of the above method, treatment periods were determined to be 5 and 10 days, and then the effects of such period for treatment with the endophytes on rice blast resistance were analyzed.

In addition, Benzisothiazole (BIT) shown in Table 7 is an active metabolite of Probenazole, which is an anti-rice-blast agricultural chemical. In rice plants treated with BIT (0.5 mg/pot), strong rice blast resistance is induced. In this experiment, a BIT treatment block was provided as a positive control for comparison with blocks of plants treated with the endophytes in terms of the effects of inducing rice blast resistance.

3. To examine the effects of nutritional conditions on disease resistance that is induced by the endophytes, three-staged fertilizer concentrations, 0.5%, 0.75%, and 1%, were determined. Rice plants in the 3-leaf stage were transplanted. Two (2) days later, treatment with endophyte suspensions was performed; and 5 days later, rice plants were inoculated with blast fungi. Rice blast resistance was then evaluated.

(Results)

In the block of plants treated with $10^8$ CFU/ml novel bacterium belonging to the genus *Azospirillum* and the block of plants treated with $10^8$ CFU/ml novel bacterium belonging to the genus *Herbaspirillum*, preventive values against blast fungi were found to be approximately 52% and 55%, respectively (Table 6). Furthermore, no differences due to periods (5 and 10 days) for treatment with the endophytes were found in the effects of inducing rice blast resistance (Table 7). In a block of plants treated with a 0.5% fertilizer solution, disease resistance induced by the endophytes was not observed; however, under conditions of 0.75% and 1% fertilizer solutions and sufficient nutrients, the effects of the endophytes to impart disease resistance were confirmed (Table 8).

TABLE 6

| | Preventive value with respect to no-treatment block |
|---|---|
| Concentration of *Azospirillum* (cfu/ml) | |
| $10^5$ | 39% |
| $10^6$ | 40% |
| $10^7$ | 30% |
| $10^8$ | 52% |
| $10^9$ | 37% |
| Concentration of *Herbaspirillum* (cfu/ml) | |
| $10^5$ | 40% |
| $10^6$ | 39% |
| $10^7$ | 23% |
| $10^8$ | 55% |
| $10^9$ | 22% |

TABLE 7

| Treatment block | Treatment period | Preventive value with respect to no-treatment block |
|---|---|---|
| BIT | 5 days | 81% |
| *Azospirillum* $10^8$ (cfu/ml) | 5 days | 59% |
| *Azospirillum* $10^8$ (cfu/ml) | 10 days | 58% |
| *Herbaspirillum* $10^8$ (cfu/ml) | 5 days | 30% |
| *Herbaspirillum* $10^8$ (cfu/ml) | 10 days | 38% |

TABLE 8

| Treatment conditions | Fertilizer concentration | Preventive value with respect to no-treatment block |
|---|---|---|
| *Azospirillum* $10^8$ (cfu/ml) 10 days | 0.5% | 0% |
| | 0.75% | 31% |
| | 1.0% | 33% |
| *Herbaspirillum* $10^8$ (cfu/ml) 10 days | 0.5% | 0% |
| | 0.75% | 33% |
| | 1.0% | 39% |

Example 6

Effects of the Novel Bacterium Belonging to the Genus *Azospirillum* or the Novel Bacterium Belonging to the Genus *Herbaspirillum* to Induce Disease Resistance Against Bacterial Disease in *Arabidopsis*

(Purpose)

In this example, the effects of inducing disease resistance against pathogenic bacteria (*Pseudomonas syringae* pv. tomato DC3000) that infect *Arabidopsis* were verified with the use of *Arabidopsis* (*Arabidopsis thaliana* Col-0) infected with the endophytes. *Arabidopsis* is a dicotyledonous model plant.

(Experimental Method)

*Arabidopsis* seeds were sterilized with 70% ethanol for 20 seconds, sterilized with a 1% hypochlorous acid aqueous solution for 5 minutes, and then washed for 20 minutes (3 times) with sterilized distilled water. Approximately 20 sterilized seeds were sown in each plastic container (5×5×5 cm) containing garden soil (Kureha) that had been autoclaved (121° C., 40 minutes), followed by cultivation within an artificial climate system under conditions of a temperature of 21° C., 60% humidity, and 16-hour light/8-hour dark.

1) Effects of the Concentrations of the Endophytes for Treatment on the Effects of Inducing Disease Resistance

*Arabidopsis* plants on week 4 after seeding were subjected to affusion using a solution of the novel bacterium belonging to the genus *Azospirillum* with a concentration between $10^6$ and $10^8$ CFU/ml. On day 5 after treatment with the endophytes, inoculation with Pst DC3000 ($1\times10^7$ CFU/ml) was performed. Five (5) days later, disease symptoms on the leaves were compared with those on control leaves.

2) Effects of the Periods for Treatment with the Endophytes on the Effects of Inducing Disease Resistance

*Arabidopsis* plants on week 3 after seeding were subjected to affusion using a bacterial suspension of the novel bacterium belonging to the genus *Azospirillum* or a bacterial suspension of the novel bacterium belonging to the genus *Herbaspirillum*, so that the concentration was $10^7$ CFU/ml. On days 10 and 15 after treatment with the endophytes, inoculation with Pst DC3000 ($1\times10^7$ CFU/ml) was performed. Five (5) days later, disease symptoms on the leaves were compared with those on control leaves.

3) Effects of Treatment with the Endophytes on the Growth of Pst DC3000

Figure 4:
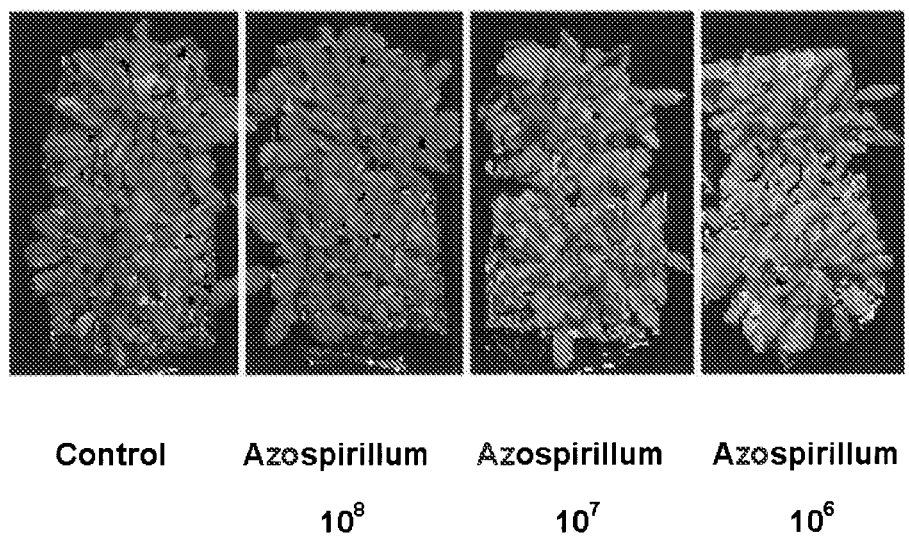
FIG. 4 shows photographs showing the effects of controlling bacterial disease exerted in *Arabidopsis* by the novel bacterium belonging to the genus *Azospirillum*.
Figure 5:
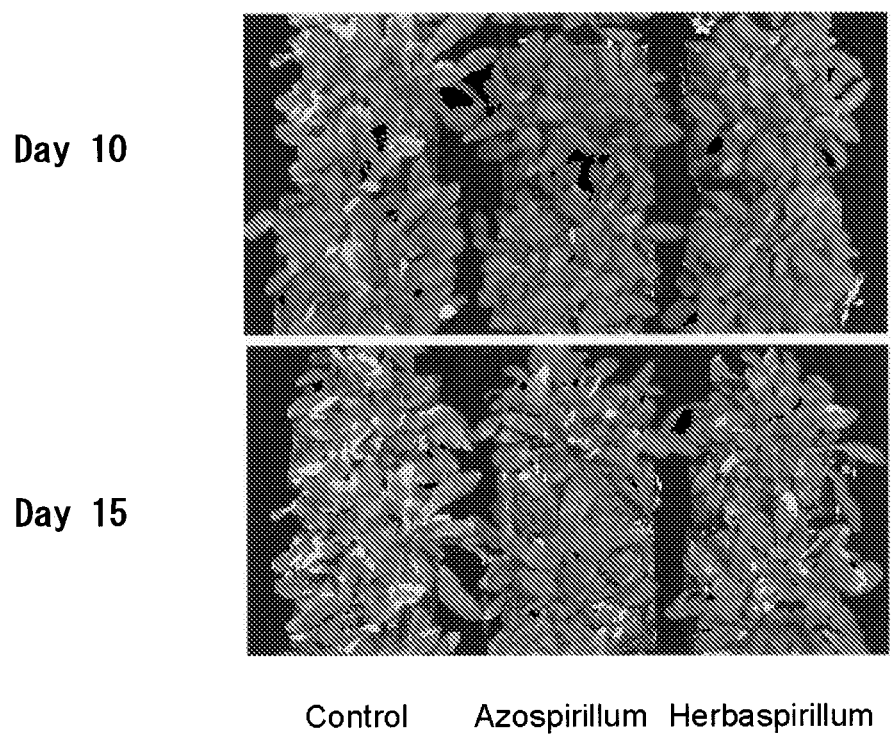
FIG. 5 shows photographs showing the effects of controlling bacterial disease in *Arabidopsis* exerted by the novel bacterium belonging to the genus *Azospirillum* and the novel bacterium belonging to the genus *Herbaspirillum*.

*Arabidopsis* plants on week 3 after seeding were subjected to affusion in the same manner as described above using the bacterial suspension so that the concentration was $10^7$ or $10^8$ CFU/ml. On day 15 after treatment, inoculation with Pst DC3000 ($2\times10^5$ CFU/ml) was performed. Leaves were collected on day 3 after inoculation and then grounded down in 10 mM $MgCl_2$. The solution obtained via grinding was diluted to three different levels. NB plate media (rifanpicin (50 mg/l)) were coated with the diluted solutions. After culturing for two nights at 28° C., colonies were counted and then the propagation rates of the bacteria within plants were quantified.
(Results)
1) As a result of treatment with the novel bacterium belonging to the genus *Azospirillum* with concentrations ranging from $10^6$ to $10^8$ CFU/ml, a tendency was confirmed such that the higher the concentration of the endophyte for treatment, the more suppressed the disease symptoms due to Pst DC3000 (FIG. 4).
2) In the block of plants treated with the novel bacterium belonging to the genus *Azospirillum*, a tendency was observed such that the longer the treatment period, the higher the effect of suppressing disease symptoms due to Pst DC3000.
In the blocks of plants treated with the novel bacterium belonging to the genus *Herbaspirillum*, almost no differences were observed in terms of the effect of suppressing disease symptoms due to Pst DC3000, even when treatment periods had differed (FIG. 5).
3) The growth of Pst DC3000 within plants was measured. Pst DC3000 growth was suppressed to a greater extent in the block of plants treated with the endophytes than that in control plants. Treatment with $10^7$ CFU/ml endophytes was found to exert stronger effects of suppressing the growth of pathogenic bacteria than treatment with $10^8$ CFU/ml endophytes (Table 9).

TABLE 9

| Treatment block | Treatment period | Preventive value with respect to no-treatment block |
| --- | --- | --- |
| *Azospirillum* $10^7$ (cfu/ml) | 15 days | 82% |
| *Azospirillum* $10^8$ (cfu/ml) | 15 days | 42% |
| *Herbaspirillum* $10^7$ (cfu/ml) | 15 days | 70% |
| *Herbaspirillum* $10^8$ (cfu/ml) | 15 days | 62% |

Example 7

Effects of the Novel Bacterium Belonging to the Genus *Azospirillum* to Induce Disease Resistance Against Fugal Disease in Komatsuna (*Brassica chinensis*)

(Purpose)
The effects of inducing disease resistance against white rust caused by a fungus (*Albugo macrospora*) were verified using komatsuna (*Brassica chinensis*) infected with the endophyte.
(Experimental Method)
(1) Culture of the Endophyte and a Method for Preparing a Bacterial Suspension
Hundred (100) ml of NB liquid medium contained in a 500-ml Erlenmeyer flask was inoculated with the novel bacterium belonging to the genus *Azospirillum*, followed by 30 hours of shake culture at 28° C. Bacterial cells were collected by centrifugation and then suspended in a 10 mM $MgCl_2$ solution, so that a bacterial suspension with a concentration of $1 \times 10^9$ CFU/ml was prepared.
(2) Cultivation of Komatsuna (*Brassica chinensis*) Seedlings and Treatment with the Endophyte
Komatsuna (*Brassica chinensis*) (cultivar: Natsurakuten (Takii Co., Ltd.)) seedlings were planted one by one on a 200-well cell tray (soil prepared for cultivation: clay soil and the amount thereof: 20 mL/well), followed by cultivation within a greenhouse. The base portions of seedlings on day 4 after seeding were treated so that the final concentration of the endophyte solution was $5 \times 10^7$ CFU/ml. After cultivation had been continued for 2 weeks within the greenhouse, plants were planted in an outdoor agricultural field (with planting intervals of 5 cm and interrow spaces of 15 cm).
(3) Onset of White Rust and Study Thereof.
The onset of white rust was observed on week 2 after planting and the following weeks. The degree of disease development was studied on week 6 after planting. The degree of disease development was evaluated with a scale of one to five: significant (5), high (4), medium (3), low (2), and extremely low (1). After statistical processing, the degree of disease development (%) was calculated.
(Results)
The degree of disease development in the block of plants treated with the novel bacterium belonging to the genus *Azospirillum* was 18.8, which was significantly lower than the degree of disease development in the block of plants not treated with the endophyte (21.8). Therefore, it was demonstrated that treatment with the novel bacterium belonging to the genus *Azospirillum* induces resistance against white rust in komatsuna (*Brassica chinensis*).

TABLE 10

Degree of white rust development

| Treatment block | Degree of white rust development |
| --- | --- |
| Novel bacterium belonging to the genus *Azospirillum* | 18.8 a |
| Control | 21.8 b |

INDUSTRIAL APPLICABILITY

The present invention provides the bacteria capable of imparting resistance against pathogenic fungal, pathogenic bacterial, or pathogenic viral disease to host plants, the method for controlling disease in plants using the bacteria, and plants produced by the method, so as to have resistance against such disease.
All publications, patents, and patent applications cited herein are incorporated herein by reference in their entirety.

The invention claimed is:

1. A method for controlling a fungal or bacterial disease in a plant, comprising:

infecting a plant with at least one isolated or purified bacterial strain selected from the group consisting of *Azospirillum* deposited under National Institute of Technology and Evaluation Patent and Microorganisms Depository (NPMD) Accession No. NITE BP-194 and *Herbaspirillum* deposited under NPMD Accession No. NITE BP-193.

2. The method according to claim 1, wherein said plant belongs to the family Gramineae.

3. The method according to claim 1, wherein said plant belongs to the family Brassicaceae.

4. The method according to claim 1, wherein said infecting occurs during a vegetative stage of said plant.

5. A composition comprising at least one isolated or purified bacterial strain selected from the group consisting of *Azospirillum* deposited under NPMD Accession No. NITE BP-194 and *Herbaspirillum* deposited under NPMD Accession No. NITE BP-193 in an amount sufficient to treat a plant disease caused by a fungus or bacterium.

6. The composition of claim 5 that is in the form of a powder, wettable powder, emulsion, solution, flowable agent, or coating agent.

7. A plant that has been infected with at least one isolated or purified bacterial strain selected from the group consisting of *Azospirillum* deposited under NPMD Accession No. NITE BP-194 and *Herbaspirillum* deposited under NPMD Accession No. NITE BP-193.

8. The plant of claim 7 that has been infected with *Azospirillum* deposited under NPMD Accession No. NITE BP-194.

9. The plant of claim 7 that has been infected with *Herbaspirillum* deposited under NPMD Accession No. NITE BP-193.

10. The method of claim 1 that is a method for controlling a fungal disease.

11. The method of claim 1 that is a method for controlling a bacterial disease.

12. The method of claim 1 that comprises infecting a plant that is a seedling.

13. The composition of claim 5 that comprises *Azospirillum* deposited under NPMD Accession No. NITE BP-194 in an amount sufficient to treat a plant disease caused by a fungus or bacterium.

14. The composition of claim 5 that comprises *Herbaspirillum* deposited under NPMD Accession No. NITE BP-193 in an amount sufficient to treat a plant disease caused by a fungus or bacterium.

* * * * *

SEQUENCE LISTING

<160> NUMBER OF SEQ ID NOS: 14

<210> SEQ ID NO 1
<211> LENGTH: 1429
<212> TYPE: DNA
<213> ORGANISM: Azospirillum sp.

```
<400> SEQUENCE: 1
aacgctggcg gcatgcctaa cacatgcaag tcgaacgatg gcttcggcca tagtggcgca      60
cgggtgagta acacgtggga acctgccttt cggttcggaa taacgtctgg aaacggacgc     120
taacaccgga tacgcccttt tggggaaagt ttacgccgag agaggggccc gcgtcggatt     180
aggtagttgg tgtggtaacg gcgcaccaag ccgacgatcc gtagctggtc tgagaggatg     240
atcagccaca ctgggactga gacacggccc agactcctac gggaggcagc agtggggaat     300
attggacaat gggcgcaagc ctgatccagc aatgccgcgt gagtgatgaa ggccttaggg     360
ttgtaaagct ctttcgcacg cgacgatgat gacggtagcg tgagaagaag ccccggctaa     420
cttcgtgcca gcagccgcgg taatacgaag ggggctagcg ttgttcggaa ttactgggcg     480
taaagggcgc gtaggcggcc ttgtcagtca gaagtgaaag ccccgggctc aacctgggaa     540
ccgcttttga tactgcaagg cttgagttcc ggagaggatg gtggaattcc cagtgtagag     600
gtgaaattcg tagatattgg gaagaacacc ggtggcgaag gcggccatct ggacggacac     660
tgacgctgag gcgcgaaagc gtggggagca acaggatta gatacctgg tagtccacgc      720
cgtaaacgat gaatgctaga cgtcggggtg catgcacttc ggtgtcgccg ctaacgcatt     780
aagcattccg cctggggagt acggccgcaa ggttaaaact caaaggaatt gacggggggcc    840
cgcacaagcg gtggagcatg tggtttaatt cgaagcaacg cgcagaacct taccaaccct     900
tgacatgtcc actatgggct tgagagatca ggtccttcgg ttcggccggg tggaacacag     960
gtgctgcatg gctgtcgtca gctcgtgtcg tgagatgttg ggttaagtcc cgcaacgagc    1020
gcaaccccta ccgtcagttg ccatcattca gttgggcact ctggtggaac cgccggtgac    1080
aagccggagg aaggcgggga tgacgtcaag tcctcatggc ccttatgggt tgggctacac    1140
acgtgctaca atggcggtga cagtgggaag cgaagtcgcg agatggagcc aatccccaaa    1200
agccgtctca gttcggatcg tactctgcaa ctcgagtgcg tgaagttgga atcgctagta    1260
atcgcggatc agcacgccgc ggtgaatacg ttcccgggcc ttgtacacac cgcccgtcac    1320
accatgggag ttggctttac ccgaagacgg tgcgctaacc cgcaagggag gcagccggcc    1380
acggtaaggt cagcgactgg ggtgaagtcg taacaaggta gccgtaggg                1429

<210> SEQ ID NO 2
<211> LENGTH: 1477
<212> TYPE: DNA
<213> ORGANISM: Herbaspirillum sp.

<400> SEQUENCE: 2
acgctggcgg catgccttac acatgcaagt cgaacggcag cataggagct tgctcctgat      60
ggcgagtggc gaacgggtga gtaatatatc ggaacgtgcc ctagagtggg ggataactag     120
tcgaaagact agctaatacc gcatacgatc taaggatgaa agtggggggat cgcaagacct    180
catgctcctg gagcggccga tatctgatta gctagttggt ggggtaaaag cctaccaagg     240
cgacgatcag tagctggtct gagaggacga ccagccacac tgggactgag acacggccca     300
gactcctacg ggaggcagca gtggggaatt ttggacaatg gggcaaccc tgatccagca      360
atgccgcgtg agtgaagaag gccttcgggt tgtaaagctc ttttgtcagg aagaaacgg      420
tagtagctaa tatctattac taatgacggt acctgaagaa taagcaccgg ctaactacgt     480
gccagcagcc gcggtaatac gtagggtgca agcgttaatc ggaattactg ggcgtaaagc     540
gtgcgcaggc ggttgtgtaa gacagatgtg aaatccccgg gctcaacctg gaattgcat     600
ttgtgactgc acggctagag tgtgtcagag gggggtagaa ttccacgtgt agcagtgaaa     660
```

```
tgcgtagata tgtggaggaa taccgatggc gaaggcagcc ccctgggata acactgacgc    720
tcatgcacga aagcgtgggg agcaaacagg attagatacc ctggtagtcc acgccctaaa    780
cgatgtctac tagttgtcgg gtcttaattg acttggtaac gcagctaacg cgtgaagtag    840
accgcctggg gagtacggtc gcaagattaa aactcaaagg aattgacggg gacccgcaca    900
agcggtggat gatgtggatt aattcgatgc aacgcgaaaa accttaccta cccttgacat    960
ggtcggaatc ctgaagagat ttaggagtgc tcgaaagaga accggcgcac aggtgctgca   1020
tggctgtcgt cagctcgtgt cgtgagatgt tgggttaagt cccgcaacga gcgcaaccct   1080
tgtcattagt tgctacgaaa gggcactcta atgagactgc cggtgacaaa ccggaggaag   1140
gtggggatga cgtcaagtcc tcatggccct tatgggtagg gcttcacacg tcatacaatg   1200
gtacatacag agggccgcca acccgcgagg ggagctaat cccagaaagt gtatcgtagt    1260
ccggattgta gtctgcaact cgactacatg aagttggaat cgctagtaat cgcggatcag   1320
catgtcgcgg tgaatacgtt cccgggtctt gtacacaccg cccgtcacac catgggagcg   1380
ggttttacca gaagtgggta gcctaaccgc aaggagggcg ctcaccacgg taggattcgt   1440
gactggggtg aagtcgtaac aaggagccgt atcggaa                             1477

<210> SEQ ID NO 3
<211> LENGTH: 659
<212> TYPE: DNA
<213> ORGANISM: Azospirillum sp.

<400> SEQUENCE: 3
ggctggatca cctcctttct aaggaagccg accttgaggg tccggcatca ggaagtccgt     60
atggcgtttc tctgccgccg ccggcgcatc ccttctcacg gttctcgacg tgctccacga    120
tggggcacgg acgggctagt agctcagttg gttagagcgc gcgcttgata agcgtgaggt    180
cggaggttca aatcctccct ggcgcaccat gtttagcggt cgtgcgtttt gccgatcggg    240
ggcatagctc agttgggaga gcgcctgctt tgcaagcagg aggtcgtcgg ttcgatcccg    300
tctgcctcca ccagtttccg gaaggagtgc tggtgtcgag ggacgctgaa ccgcccagct    360
tcgaggaccg ttggaaggaa ccacaacacg gcaacgtgaa cagccacgag cgcttcgcgc    420
tcgttgctgt gtccctcacg ggacgggatc atggacaagt gaagatgaag tgcaagtgac    480
cgaggacgct cctcggccgg caagcccaca aggcgacgct ggctgggagc agcatcgaac    540
ggcggaaaca gctggctagc taccagctcg cgagcaggct tgttcctgcg cgtggcgcaa    600
gcgttttcgt tggagttgag atcaagcgtc tgaagggcat ctggtggatg ccttgggca    659

<210> SEQ ID NO 4
<211> LENGTH: 624
<212> TYPE: DNA
<213> ORGANISM: Herbaspirillum sp.

<400> SEQUENCE: 4
ggctggatca cctcctttct agagtgcgca cgaagttaag cgtccacact tctcggctgt     60
aattcaaaga acagttattt ggtgaagcgc ggtccgtgac acaaggtcac tgactggcta    120
ctgatactga tccaagcggg tctgtagctc agctggttag agcaccgtgt tgataacgcg    180
ggggtcgttg gttcgagccc aaccagaccc accaaggttt cggggggttta gctcagctgg    240 gagagcacct gctttgcaag caggggggtcg tcggttcgat cccgtcaacc tccaccaaga    300
aatgtcaaac ctaagtcagc gtcacaaaac gcaagacgta gtgatttagg tttgatcttt    360
tatgatcaat ggctgttttt gttctttaac aatctggaag aagtaaagat tcatttaaac    420
```

```
gatcgccagg acttcggttc ttgcgaaagt aaaaatgggt gtgattgtat caatcaaagt      480
attacgaagt gatcttagca attagaagac ttgctttgga atacggcaaa cgctaaaact      540
caacgcttct ttataacgct cttgcaaaag aggctaacgt tataggaaca agcgaataac      600
tgcacatggt ggatgccttg ggca                                             624
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
ttgagggtcc ggcatcag                                                    18

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tcaggaagtc cgtatggcgt t                                                21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
cgtccctcga caccagcac                                                   19

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gtcgccttgt gggcttgc                                                    18

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gcggtccgtg acacaa                                                      16

<210> SEQ ID NO 10
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 10
caaggtcact gactggctac tg                                              22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cactacgtct tgcgttttgt g                                               21

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgcaagaacc gaagtcct                                                   18

<210> SEQ ID NO 13
<211> LENGTH: 1477
<212> TYPE: DNA
<213> ORGANISM: Azospirillum sp.

<400> SEQUENCE: 13
agagtttgat catggctcag aacgaacgct ggcggcatgc ctaacacatg caagtcgaac      60
gaaggcttcg gccttagtgg cgcacgggtg agtaacacgt gggaacctgc ctttcggttc     120
ggaataacgt ctggaaatgg acgctaacac cggatacgcc ctattgggga agtttacgc     180 cgagagaggg gcccgcgtcg gattaggtag ttggtgtggt aacggcgctc caagccgacg     240
atccgtagct ggtctgagag gatgatcagc cacactggga ctgagacacg gcccagactc     300
ctacgggagg cagcagtggg gaatattgga caatgggcgc aagcctgatc cagcaatgcc     360
gcgtgagtga tgaaggcctt agggttgtaa agctctttcg cacgcgacga tgatgacggt     420
agcgtgagaa gaagccccgg ctaacttcgt gccagcagcc gcggtaatac gaaggggct     480 agcgttgttc ggaattactg ggcgtaaagg cgcgtaggc ggcctgttta gtcagaagtg     540
aaagccccgg gctcaacctg gaatagcctt ttgatactgg caggcttgag ttccggagag     600
gatggtggaa ttcccagtgt agaggtgaaa ttcgtagata ttgggaagaa caccggtggc     660
gaaggcggcc atctggacgg acactgacgc tgaggcgcga aagcgtgggg agcaaacagg     720
attagatacc ctggtagtcc acgccgtaaa cgatgaatgc tagacgtcgg ggtgcatgca     780
cttcggtgtc gccgctaacg cattaagcat tccgcctggg gagtacggcc gcaaggttaa     840
aactcaaagg aattgacggg ggcccgcaca agcggtggag catgtggttt aattcgaagc     900
aacgcgcaga accttaccaa cccttgacat gtccactatg gcttcagag atgaggtcct      960 tcggttcggc cggtggaac acaggtgctg catggctgtc gtcagctcgt gtcgtgagat     1020
gttgggttaa gtcccgcaac gagcgcaacc cctaccgtca gttgccatca ttcagttggg     1080
cactctggtg gaaccgccgg tgacaagccg gaggaaggcg gggatgacgt caagtcctca     1140
```

-continued

```
tggcccttat gggttgggct acacacgtgc tacaatggcg gtgacagtgg gaggcgaagt    1200
cgcgagatgg agcaaatccc caaaagccgt ctcagttcgg attgcactct gcaactcgag    1260
tgcatgaagt tggaatcgct agtaatcgcg gatcagcacg ccgcggtgaa tacgttcccg    1320
ggccttgtac acaccgcccg tcacaccatg ggagttggct ttacccgaag acggtgcgct    1380
aaccggcaac ggaggcagcc ggccacggta aggtcagcga ctggggtgaa gtcgtaacaa    1440
ggtagccgta ggggaacctg cggctggatc acctcct                            1477

<210> SEQ ID NO 14
<211> LENGTH: 1485
<212> TYPE: DNA
<213> ORGANISM: Herbaspirillum rubrisubalbicans

<400> SEQUENCE: 14
attgaacgct ggcggcatgc cttacacatg caagtcgaac ggcagcatag gagcttgctc      60
ctgatggcga gtggcgaacg ggtgagtaat atatcggaac gtgccctaga gtgggggata    120
actagtcgaa agactagcta ataccgcata cgatctaagg atgaaagtgg gggatcgcaa    180
gacctcatgc tcctggagcg gccgatatct gattagctag ttggtggggt aaaagcctac    240
caaggcgacg atcagtagct ggtctgagag gacgaccagc cacactggga ctgagacacg    300
gcccagactc ctacgggagg cagcagtggg gaattttgga caatggggc aaccctgatc    360 cagcaatgcc gcgtgagtga agaaggcctt cgggttgtaa agctcttttg tcagggaaga    420
aacggtggta gctaatatct actactaatg acggtacctg aagaataagc accggctaac    480
tacgtgccag cagccgcggt aatacgtagg gtgcaagcgt taatcggaat tactgggcgt    540
aaagcgtgcg caggcggttg tgtaagtcag atgtgaaatc cccgggctca acctgggaat    600
tgcatttgag actgcacggc tagagtgtgt cagaggggg tagaattcca cgtgtagcag    660
tgaaatgcgt agatatgtgg aggaataccg atggcgaagg cagcccctg ggataacact    720 gacgctcatg cacgaaagcg tggggagcaa acaggattag ataccctggt agtccacgcc    780
ctaaacgatg tctactagtt gtcgggtctt aattgacttg gtaacgcagc taacgcgtga    840
agtagaccgc ctggggagta cggtcgcaag attaaaactc aaaggaattg acggggaccc    900
gcacaagcgg tggatgatgt ggattaattc gatgcaacgc gaaaaacctt acctaccctt    960
gacatggtcg gaatcctgaa gagatttggg agtgctcgaa agagaaccgg cgcacaggtg    1020
ctgcatggct gtcgtcagct cgtgtcgtga gatgttgggt taagtcccgc aacgagcgca    1080
acccttgtca ttagttgcta cgaaagggca ctctaatgag actgccggtg acaaaccgga    1140
ggaaggtggg gatgacgtca agtcctcatg gcccttatgg gtagggcttc acacgtcata    1200
caatggtaca tacagagggc cgccaacccg cgaggggggag ctaatcccag aaagtgtatc    1260
gtagtccgga ttgtagtctg caactcgact acatgaagtt ggaatcgcta gtaatcgcgg    1320
atcagcatgt cgcggtgaat acgttcccgg gtcttgtaca caccgcccgt cacaccatgg    1380
gagcgggttt taccagaagt gggtagccta accgcaagga gggcgctcac cacggtagga    1440
ttcgtgactg gggtgaagtc gtaacaaggt agccgtatcg gaagg                   1485
```